United States Patent [19]

Condon et al.

[11] 4,293,481

[45] Oct. 6, 1981

[54] TRIPEPTIDE INHIBITORS OF ANGIOTENSIN-CONVERTING ENZYME

[75] Inventors: Michael E. Condon, Lawrenceville; Miguel A. Ondetti, Princeton, both of N.J.

[73] Assignee: E. R. Squibb & Sons, Inc., Princeton, N.J.

[21] Appl. No.: 171,772

[22] Filed: Jul. 24, 1980

[51] Int. Cl.³ ............................................. C07C 103/52
[52] U.S. Cl. .......................... 260/112.5 R; 260/326.35; 260/326.36
[58] Field of Search ................... 260/112.5 R, 326.35, 260/326.36

[56] References Cited

U.S. PATENT DOCUMENTS 4,191,753  3/1980  Ryan ............................. 260/112.5 R

*Primary Examiner*—Delbert R. Phillips
*Attorney, Agent, or Firm*—Lawrence S. Levinson; Donald J. Barrack

[57] ABSTRACT

Peptides having the formula

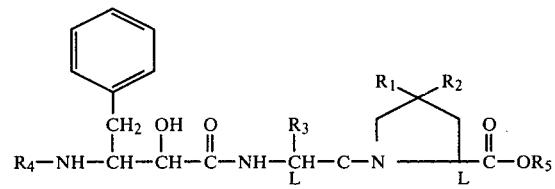

wherein
$R_1$ is hydrogen and $R_2$ is hydroxyl, alkyl, aryl, arylalkyl, alkoxy, alkylthio, aryloxy, arylthio, halogen or azido, or $R_1$ and $R_2$ are the same and each is hydrogen, halogen, alkoxy or alkylthio, or $R_1$ and $R_2$ together are oxo, $-O-(CH_2)_n-O-$, or $-S-(CH_2)_n-S-$, wherein n is 1 or 2;
$R_3$ is hydrogen, alkyl or trifluoromethyl;
$R_4$ is hydrogen or an acyl protecting group; and
$R_5$ is hydrogen or alkyl;
are inhibitors of angiotensin converting enzyme and can be used for the treatment of hypertension in mammals.

7 Claims, No Drawings

4,293,481

TRIPEPTIDE INHIBITORS OF ANGIOTENSIN-CONVERTING ENZYME

BACKGROUND OF THE INVENTION

Nishizawa et al., *Journal of Medicinal Chemistry*, 20(4):510 (1977) have synthesized, and studied the activity of [(2S,3R)-3-amino-2-hydroxy-4-phenylbutanoyl]-L-leucine (bestatin) and analogs. Bestatin has the structural formula

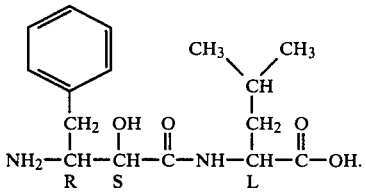

Many analogs of bestatin are reported in the reference. Among the analogs disclosed is the compound wherein L-alanine is substituted for the L-leucine moiety of bestatin. Bestatin is disclosed to be an inhibitor of aminopeptidase B and leucine aminopeptidase.

U.S. Pat. No. 3,832,337, issued Aug. 27, 1974 deals with peptides and acylated peptides that inhibit the conversion of angiotensin I into angiotensin II.

Recently many compounds falling into the general category of mercaptoacylamino acids have been found to be useful as inhibitors of angiotensin converting enzyme. The most well known of these compounds, captopril (D-(3-mercapto-2-methyl-1-oxopropyl)-L-proline) is currently being developed as a treatment for hypertension. Captopril is disclosed in U.S. Pat. No. 4,105,776.

U.S. Pat. No. 4,191,753 discloses peptides having the sequence

<Glu-Trp-A₃-Arg-A₅-Gln-Ile-A₈-A₉ wherein $A_3$, $A_5$, $A_8$ and $A_9$ each is L-proline or L-3,4-dihydroproline. The peptides are angiotensin converting enzyme inhibitors.

Dipeptides having the formula

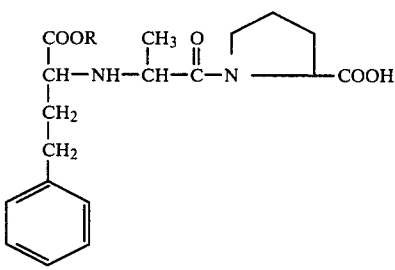

have also been disclosed as useful inhibitors of angiotensin converting enzyme; Patchett et al., 17th National Medicinal Chemistry Symposium, June 15–19, 1980, Troy, New York. The compound of the above formula wherein R is ethyl is currently being developed as a treatment for hypertension.

BRIEF DESCRIPTION OF THE INVENTION

Novel tripeptides having the formula

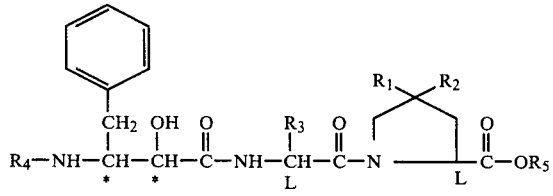

are useful compounds. In formula I, and throughout the specification, the symbols are as defined below.

$R_1$ is hydrogen and $R_2$ is hydroxyl, alkyl, aryl, arylalkyl, alkoxy, alkylthio, aryloxy, arylthio, halogen, or azido, or $R_1$ and $R_2$ are the same and each is hydrogen, halogen, alkoxy or alkylthio, or $R_1$ and $R_2$ together are oxo, $-O-(CH_2)_n-O-$, or $-S-(CH_2)_n-S-$, wherein n is 1 or 2;

$R_3$ is hydrogen, alkyl or trifluoromethyl;

$R_4$ is hydrogen or an acyl protecting group such as arylalkoxycarbonyl or alkoxycarbonyl; and $R_5$ is hydrogen or alkyl. The compounds of formula I wherein $R_4$ and $R_5$ are hydrogen inhibit the action of angiotensin converting enzyme and are useful for lowering blood pressure. The compounds of formula I wherein $R_4$ or $R_5$ is other than hydrogen are useful intermediates.

The term "aryl," as used throughout the specification either by itself or as part of a larger group, refers to phenyl or phenyl substituted with halogen, alkyl, alkoxy, alkylthio, hydroxy, alkanoyl, nitro, amino, dialkylamino, phenyl or trifluoromethyl groups. Phenyl and monosubstituted phenyl are the preferred aryl groups; phenyl is the most preferred group.

The term "alkyl," as used throughout the specification either by itself or as part of a larger group, refers to groups having 1 to 8 carbon atoms. Alkyl groups having 1 to 3 carbon atoms are preferred.

The term "alkoxy," as used throughout the specification either by itself or as part of a larger group, refers to groups having 1 to 8 carbon atoms. Alkoxy groups having 1 to 3 carbon atoms are preferred.

The term "halogen," as used throughout the specification either by itself or as part of a larger group, refers to fluorine, chlorine, bromine and iodine. The preferred halogen groups are fluorine and chlorine.

The term "alkanoyl," as used throughout the specification either by itself or as part of a larger group, refers to groups having 2 to 9 carbon atoms.

The carbon atoms marked with an asterisk in formula I are asymmetric and can exist in the S or R configuration. The four possible stereoisomers (S,S; S,R; R,S; R,R) are encompassed by this invention. For the carbon atom bearing the hydroxyl group, the S configuration is preferred.

DETAILED DESCRIPTION OF THE INVENTION

The peptides of formula I, and salts thereof, are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The peptides of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one (or a combination) of the peptides of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The peptides of this invnetion can also be formulated in combination with a diuretic for the treatment of hypertension. A combination product comprising a peptide of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combintation with a peptide of this invention are the thiazide diuretics, e.g., chlorthiazide, hydrochlorthiazide, flumethiazide, hydroflumethiazide, bendroflumethiazide, methychlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The peptides of formula I can be formulated for use in the reduction of blood pressure in compositions such as tablets, capsules or elixirs for oral administration, or in sterile solutions of suspensions for parenteral administration. About 10 to 500 mg. of a peptide or mixture of peptides of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Preparation of the peptides of this invention can be accomplished using as starting materials a compound having the formula

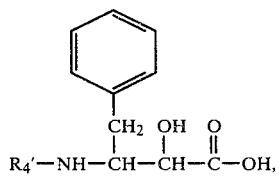

wherein $R_4'$ is an acyl protecting group such as arylalkoxycarbonyl or alkoxycarbonyl; an amino acid having the formula

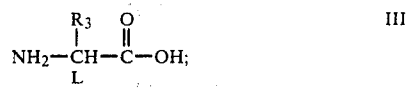

and an imino acid derivative having the formula

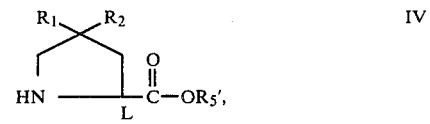

wherein $R_5'$ is alkyl.

The synthesis of the tripeptides of this invention can be accomplished by first coupling the amino acids of formulas III and IV and subsequently coupling the resulting dipeptide with an amino acid of formula II. Alternatively, amino acids of formulas II and III can be coupled first and the resulting dipeptide coupled with an amino acid of formula IV.

The above-described coupling reactions can be accomplished using known amide bond forming procedures that are conventionally used in peptide syntheses. The reaction can be run in the presence of a coupling agent such as dicyclohexylcarbodiimide, or the acid can be activated by formation of its mixed anhydride, symmetrical anhydride, acid halide (preferably acid chloride) or acid ester, or by the use of Woodward reagent K,N-ethoxycarbonyl-2-ethoxy-1,2-dihydroquinoline or the like. A review of these methods can be found in *Methoden der Organischen Chemie* (Houben-Weyl), Vol. XV, part II, page 1 et seq. (1974).

The above described reactions yield the intermediates wherein $R_4$ and $R_5$ are other than hydrogen. Removal of the nitrogen protecting group from an intermediate of formula I ($R_4$ is an acyl protecting group) can be accomplished using catalytic hydrogenation or by acid hydrolysis. The removal of the alkyl ester group from the proline group can be accomplished by standard treatment with a base such as sodium hydroxide, or if $R_5'$ is t-butyl, by reaction with trifluoroacetic acid and anisole.

The products of formula I (wherein $R_5$ is hydrogen) form basic salts with various inorganic and organic bases which are also within the scope of this invention. Such salts include ammonium salts, alkali metal salts like sodium and potassium salts, alkaline earth metal salts like the calcium and magnesium salts, salts with organic bases, e.g., dicyclohexylamine salt, benzathine, N-methyl-D-glucamine, hydrabamine salts, and salts with amino acids like arginine, lysine and the like. The non-toxic, physiologically acceptable salts are preferred, although other salts are also useful, e.g., in isolating or purifying the product. The salts can be formed using conventional techniques.

The tripeptides of formula I wherein $R_3$ is methyl are preferred.

The following examples are specific embodiments of this invention.

EXAMPLE 1

(S,S)-1-[N-(3-Amino-2-hydroxy-1-oxo-4-phenylbutyl)-L-alanyl]-L-proline

(A)

(S,S)-1-[N-[3-[(Benzyloxycarbonyl)amino]-2-hydroxy-1-oxo-4-phenylbutyl]-L-alanyl]-L-proline, t-butyl ester A mixture of (2S,3S)-3-[(benzyloxycarbonyl) amino]-2-hydroxy-4-phenylbutanoic acid (658 mg, 2 mmol), L-Ala-L-Pro t-butyl ester (580 mg, 2.4 mmol), hydroxybenzotriazole hydrate (368 mg, 2.4 mmol) and triethylamine (0.28 ml, 2 mmol) in 20 ml of tetrahydrofuran is cooled in an ice bath. While stirring the mixture, a solution of N,N'-dicyclohexylcarbodiimide (412 mg, 2 mmol) in dichloromethane (20 ml) is added dropwise in 15 minutes. The mixture is stirred for about 16 hours at room temperature. The mixture is filtered through diatomaceous earth and the filtrate is taken to dryness in vacuo. The residue is dissolved in ethyl acetate, washed twice with 10%; potassium sulfate solution, once with water, dried and freed of solvent in vacuo leaving 1.1 g of (S,S)-1-[N-[3-[benzyloxycarbonyl)-amino]-2-hydroxy-1-oxo-4-phenylbutyl]-L-alanyl]-L-proline, t-butyl ester. A small sample of this product is recrystallized from ethyl acetate to give an analytical sample, melting point 156°–165° C., $[\alpha]_D = -89.4°$ (c=0.8, methanol).

Anal. Calc'd. for $C_{30}H_{40}O_7N_3$: C, 64.96; H, 7.27; N, 7.58; Found: C, 65.02; H, 7.32; N, 7.87.

(B)

(S,S)-1-[N-[3-[(Benzyloxycarbonyl)amino]-2-hydroxy-1-oxo-4-phenylbutyl]-L-alanyl]-L-proline (S,S)-1-[N-[3-[(benzyloxycarbonyl)amino]-2-hydroxy-1-oxo-4-phenylbutyl]-L-alanyl]-L-proline, t-butyl ester (1.1 g, 2 mmol) is treated with 5 ml of anisole and 20 ml of trifluoroacetic acid. The solution is stirred at room temperature for 3 hours and taken to dryness in vacuo. Ether is added to the residue and this is extracted twice with saturated sodium bicarbonate solution. The combined sodium bicarbonate extracts are washed twice with ether and then acidified with hydrochloric acid. Three ethyl acetate extractions give 1.2 g of viscous material, which is crude (S,S)-1-[N-[3-[(t-butyloxycarbonyl)amino]-2-hydroxy-1-oxo-4-phenylbutyl]-L-alanyl]-L-proline.

(C)

(S,S)-1-[N-(3-Amino-2-hydroxy-1-oxo-4-phenyl-butyl)-L-alanyl]-L-proline

Crude (S,S)-1-[N-[3-[(benzyloxycarbonyl)amino]-2-hydroxy-1-oxo-4-phenylbutyl]-L-alanyl]-L-proline (about 2 mmol) is dissolved in 50 ml of methanol and 25 ml of water. After sweeping the system with argon 0.5 g of 10% palladium on charcoal is added. While stirring, a slow stream of hydrogen is passed over the surface for eighteen hours. The catalyst is removed by filtration through diatomaceous earth and the pad is washed with methanol. The filtrate is taken to dryness in vacuo and methanol is added four times and removed in vacuo leaving 0.65 g of a glass. This material is combined with that from another run. Most of this material is dissolved in 5 ml water and is applied to a column packed with 12 ml AG50WX2 (H+) resin. The column is eluted with water until the eluate is no longer strongly acidic and then is eluted with pH 6.5 buffer. Fractions positive to ninhydrin are pooled. It appears that some of the product has precipitated on the column so when fractions give only a very weak test with ninhydrin the remaining product is eluted with 2 N NH$_4$OH. The two pools are worked up separately by taking to dryness in vacuo and adding water and again taking to dryness. Electrophoresis on the two materials are identical; −5.3 cm (pH 1.9 buffer, 2000 V, 30 min., detected ninhydrin and I$_2$). The two pools are combined, triturated with water, the solid harvested by filtration, washed with more water and then with methanol. Drying in vacuo over P$_2$O$_5$ at 75° C. gives the analytical sample (412 mg), $[\alpha]_D = -120°$ (c=0.64, acetic acid).

Anal. Calc'd. for $C_{18}H_{25}O_5N_3$: C, 59.49; H, 6.93; N, 11.56; Found: C, 59.47; H, 7.19; N, 11.68.

EXAMPLES 2–19

Following the procedure of Examples 1, but substituting the dipeptide ester listed in column I for L-Ala-L-Pro t-butyl ester, yields the peptide listed in column II.

| Column I | Column II |
| --- | --- |
| 2. N-(L-alanyl)-4-hydroxy-L-proline, t-butyl ester | (S,S)-1-[N-(3-amino-2-hydroxy-1-oxo-4-phenylbutyl)-L-alanyl]-4-hydroxy-L-proline |
| 3. N-(L-alanyl)-4-methyl-L-proline t-butyl ester | (S,S)-1-[N-(3-amino-2-hydroxy-1-oxo-4-phenylbutyl)-L-alanyl]-4-methyl-L-proline |
| 4. N-(L-alanyl)-4-methoxy-L-proline, t-butyl ester | (S,S)-1-[N-(3-amino-2-hydroxy-1-oxo-4-phenylbutyl)--L-alanyl]-4-methoxy-L-proline |
| 5. N-(L-alanyl)-4-(methylthio)-L-proline, t-butyl ester | (S,S)-1-[N-(3-amino-2-hydroxy-1-oxo-4-phenylbutyl)-L-alanyl]-4-(methylthio-L-proline |
| 6. N-(L-alanyl)-4-phenyl-L-proline t-butyl ester | (S,S)-1-[N-(3-amino-2-hydroxy-1-oxo-4-phenylbutyl)-L-alanyl]-4-phenyl-L-proline |
| 7. N-L-alanyl)-4-(phenylthio)-L-proline, t-butyl ester | (S,S)-1-[N-(3-amino-2-hydroxy-1-oxo-4-phenylbutyl)-L-alanyl]-4-(phenylthio-L-proline |
| 8. N-(L-alanyl)-4-benzyl-L-proline, t-butyl ester | (S,S)-1-[N-(3-amino-2-hydroxy-1-oxo-4-phenylbutyl)-L-alanyl]-4-benzyl-L-proline |
| 9. N-(L-alanyl)-4-(4-fluorophenoxy)-L-proline, t-butyl ester | (S,S)-1-[N-(3-amino-2-hydroxy-1-oxo-4-phenylbutyl)-L-alanyl]-4-(fluorophenoxy)-L-proline |
| 10. N-(L-alanyl)-4-(methoxyphenylthio)-L-proline, t-butyl ester | (S,S)-1-[N-(3-amino-2-hydroxy-1-oxo-4-phenylbutyl)-L-alanyl]-4-(methoxyphenylthio)-L-proline |
| 11. N-(L-alanyl)-4-fluoro-L-proline, t-butyl ester | (S,S)-1-[N-(3-amino-2-hydroxy-1-oxo-4-phenylbutyl)-L-alanyl]-4-fluoro-L-proline |
| 12. N-(L-alanyl)-4-azido-L-proline, t-butyl ester | (S,S)-1-[N-(3-amino-2-hydroxy-1-oxo-4-phenylbutyl)-L-alanyl]-4-azido-L-proline |
| 13. N-(L-alanyl)-4,4-difluoro-L-proline, t-butyl ester | (S,S)-1-[N-(3-amino-2-hydroxy-1-oxo-4-phenylbutyl)-L-alanyl]-4,4-difluoro-L-proline |
| 14. N-(L-alanyl)-4,4-dimethoxy-L- | (S,S))-1-[N-(3-amino-2-hydroxy-1-oxo-4-phenylbutyl)- |

| Column I | Column II |
| --- | --- |
| proline, t-butyl ester | L-alanyl]-4,4-dimethoxy-L-proline |
| 15. N-(L-alanyl)-4,4-dimethylthio-L-proline, t-butyl ester | (S,S)-1-[N-(3-amino-2-hydroxy-1-oxo-4-phenylbutyl)-L-alanyl]-4,4-dimethylthio-L-proline |
| 16. N-(L-alanyl)4,4-ethylenedioxy-L-proline, butyl ester | (S,S)-1-[N-(3-amino-2-hydroxy-1-oxo-4-phenylbutyl)-L-alanyl]-4,4-ethylenedioxy-L-proline |
| 17. N-(L-alanyl)-4,4-ethylenedithio-L-proline, t-butyl ester | (S,S)-1-[N-(3-amino-2-hydroxy-1-oxo-4-phenylbutyl)-L-alanyl]-4,4-ethylenedithio-L-proline |
| 18. N-(2-amino-2-trifluoromethyl-1-oxoethyl)-L-proline, butyl ester | (S,S)-1-[N-(3-amino-2-hydroxy-1-oxo-4-phenylbutyl)-(2-amino-2-trifluoromethyl-1-oxoethyl)]-L-proline |
| 19. N-(2-amino-1-oxoethyl)-L-proline, t-butyl ester | (S,S)-1-[N-(3-amino-2-hydroxy-1-oxo-4-phenylbutyl)-(2-amino-1-oxoethyl))]-L-proline |

What is claimed is:

1. A tripeptide having the formula

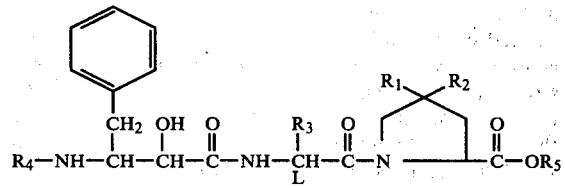

or a salt thereof, wherein $R_1$ is hydrogen and $R_2$ is hydroxyl, alkyl, aryl, arylalkyl, alkoxy, alkylthio, aryloxy, arylthio, halogen, or azido, or $R_1$ and $R_2$ are the same and each is hydrogen, halogen, alkoxy or alkylthio, or $R_1$ and $R_2$ together are oxo, $-O-(CH_2)_n-O-$, or $-S-(CH_2)_n-S-$, wherein n is 1 or 2;

$R_3$ is hydrogen, alkyl or trifluoromethyl;
$R_4$ is hydrogen or an acyl protecting group; and
$R_5$ is hydrogen or alkyl.

2. A tripeptide in accordance with claim 1 wherein $R_4$ and $R_5$ each is hydrogen.

3. A tripeptide in accordance with claim 2 wherein $R_3$ is methyl.

4. A tripeptide in accordance with claim 2 wherein $R_1$ and $R_2$ are hydrogen.

5. The tripeptide in accordance with claim 1 (S,S)-1-[N-[3-[(benzyloxycarbonyl)amino]-2-hydroxy-1-oxo-4-phenylbutyl]-L-alanyl]-L-proline, t-butyl ester.

6. The tripeptide in accordance with claim 1 (S,S)-1-[N-[3-[(benzyloxycarbonyl)amino]-2-hydroxy-1-oxo-4-phenylbutyl]-L-alanyl]-L-proline.

7. The tripeptide in accordance with claim 1 (S,S)-1-[N-(3-amino-2-hydroxy-1-oxo-4-phenylbutyl)-L-alanyl]-L-proline.

* * * * *

UNITED STATES PATENT AND TRADEMARK OFFICE
CERTIFICATE OF CORRECTION

PATENT NO. : 4,293,481
DATED : October 6, 1981
INVENTOR(S) : Michael E. Condon, et al It is certified that error appears in the above-identified patent and that said Letters Patent are hereby corrected as shown below:

In the table at the bottom of columns 5 and 6, Example 7, column I, the first line should read:  -- N-(L-alanyl)-4-(phenylthio)-L- --

In the table at the bottom of columns 5 and 6, Example 14, column II, the first line should read: -- (S,S)-1-[N-(3-amino-2-hydroxy-1-oxo-4-phenylbutyl)- --

In the table at the top of columns 7 and 8, Example 16, column I should read -- N-(L-alanyl)-4,4-ethylenedioxy-L-proline, t-butyl ester --

In the table at the top of columns 7 and 8, Example 18, column I, the second line should read: -- oxoethyl)-L-proline,t-butyl ester --

Signed and Sealed this

Ninth Day of March 1982

[SEAL]

Attest:

GERALD J. MOSSINGHOFF

*Attesting Officer*  *Commissioner of Patents and Trademarks*